(12) United States Patent
Burke

(10) Patent No.: US 8,852,233 B2
(45) Date of Patent: Oct. 7, 2014

(54) APPARATUS FOR THE CORRECTION OF SKELETAL DEFORMITIES

(76) Inventor: John Gerard Burke, Edinburgh (GB)

( * ) Notice: Subject to any disclaimer, the term of this patent is extended or adjusted under 35 U.S.C. 154(b) by 1983 days.

(21) Appl. No.: 11/628,567

(22) PCT Filed: Jun. 6, 2005

(86) PCT No.: PCT/GB2005/002210
§ 371 (c)(1),
(2), (4) Date: Dec. 11, 2007

(87) PCT Pub. No.: WO2005/117731
PCT Pub. Date: Dec. 15, 2005

(65) Prior Publication Data
US 2008/0195149 A1 Aug. 14, 2008

(30) Foreign Application Priority Data
Jun. 4, 2004 (GB) .................................. 0412503.5

(51) Int. Cl.
*A61B 17/70* (2006.01)
*A61B 17/80* (2006.01)

(52) U.S. Cl.
CPC ......... *A61B 17/8004* (2013.01); *A61B 17/7001* (2013.01); *A61B 17/701* (2013.01); *A61B 17/7025* (2013.01); *A61B 17/7044* (2013.01)
USPC ........... 606/246; 606/250; 606/251; 606/252; 606/257

(58) Field of Classification Search
USPC .................................. 606/246–279, 300–321
See application file for complete search history.

(56) References Cited

U.S. PATENT DOCUMENTS

| | | | | |
|---|---|---|---|---|
| 4,697,582 A | * | 10/1987 | William | 606/254 |
| 6,193,720 B1 | * | 2/2001 | Yuan et al. | 606/279 |
| 6,540,749 B2 | * | 4/2003 | Schafer et al. | 606/270 |
| 6,554,831 B1 | * | 4/2003 | Rivard et al. | 606/253 |
| 7,479,156 B2 | * | 1/2009 | Lourdel et al. | 606/266 |
| 2005/0038432 A1 | * | 2/2005 | Shaolian et al. | 606/61 |
| 2005/0131407 A1 | * | 6/2005 | Sicvol et al. | 606/61 |
| 2006/0247635 A1 | * | 11/2006 | Gordon et al. | 606/61 |

FOREIGN PATENT DOCUMENTS

| | | |
|---|---|---|
| FR | 2709245 | 3/1995 |
| WO | WO 0217803 | 3/2002 |
| WO | WO 0243602 | 6/2002 |
| WO | WO 02053038 | 7/2002 |

\* cited by examiner

*Primary Examiner* — Pedro Philogene
*Assistant Examiner* — Christina Negrellirodrigue
(74) *Attorney, Agent, or Firm* — Kinney & Lange, P.A.

(57) ABSTRACT

An implantable apparatus for use in the correction of skeletal deformities comprising a rod, a pair of spaced apart attachment members, each of the attachment members being attachable to a bone. At least one of the attachment member mounts a rod receiving member, the rod being slidable along a predetermined path with respect to the rod receiving member.

15 Claims, 10 Drawing Sheets

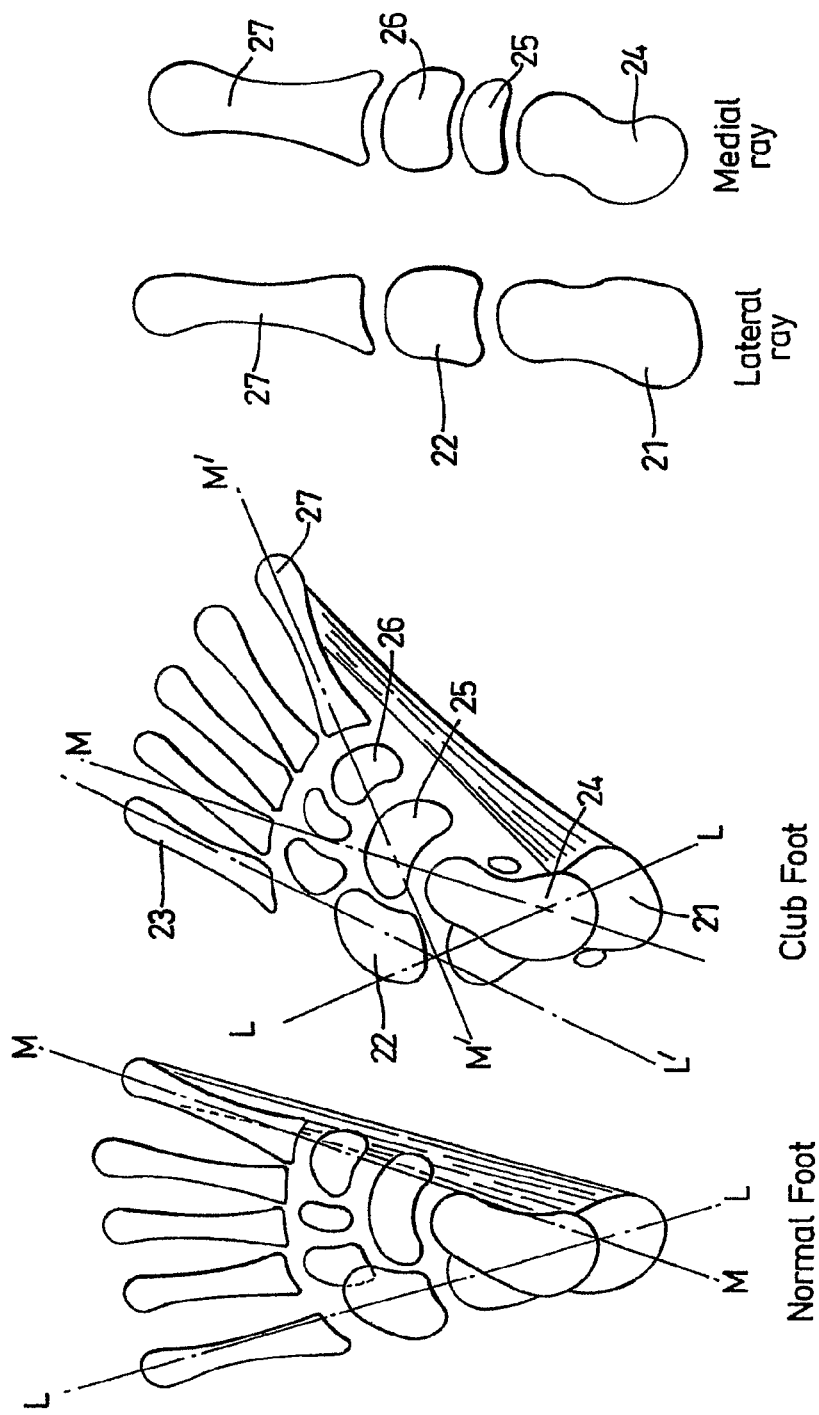

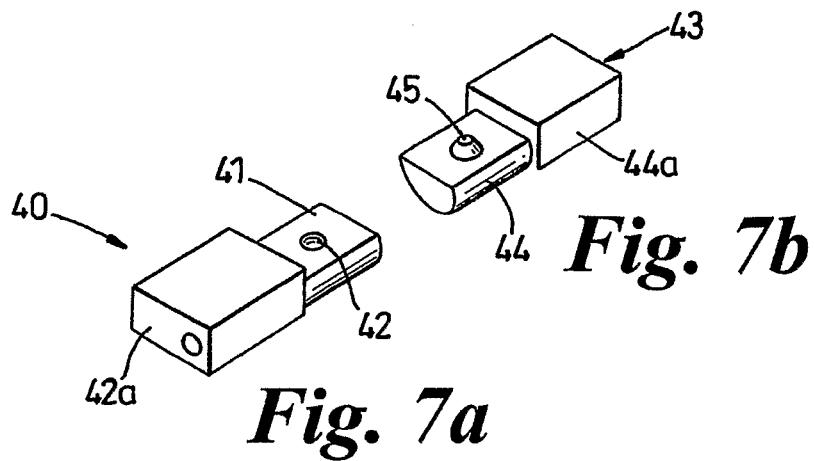
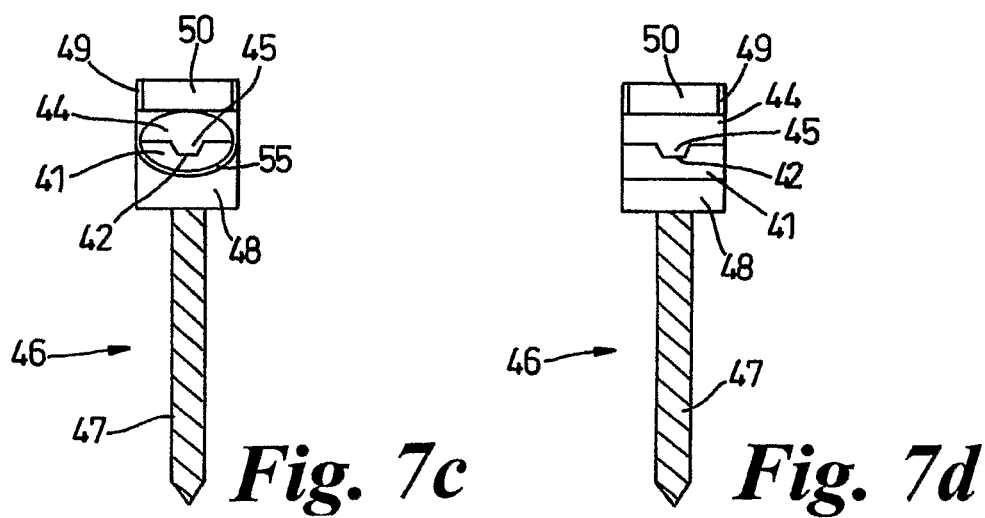
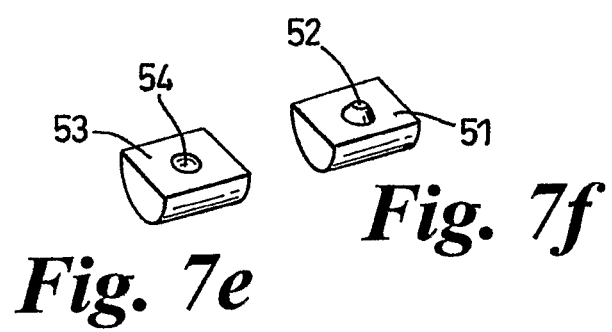

APPARATUS FOR THE CORRECTION OF SKELETAL DEFORMITIES

FIELD OF THE INVENTION

The invention relates to apparatus for correcting skeletal deformities, and in particular to an implantable device for controlling the relationship of bones on either side of a growth plate in paediatrics, and in adults to assist in holding bones in a locked configuration.

BACKGROUND OF THE INVENTION

A number of conditions give rise to paediatric deformity, for example scoliosis (or curvature of the spine), club foot, post traumatic deformity such as cubitus varus, knock knees, etc.

Early onset scoliosis is currently managed conservatively with the use of localiser casts and braces to delay curve progression until the child is old enough for definitive treatment by instrumentation and fusion of the curve. Where conservative therapy fails, a variety of surgical procedures are used. For example, convex epiphysiodesis, stapling of the convex side of the curve, short segment fusion, and posterior growing rod systems such as the Harrington rod, ISOLA® growing rods or the Luque trolley system.

The Luque trolley system is described in French published patent application No 2589716 comprises a pair of U-shaped callipers fixed to the spine, one of the callipers sliding within the other so that the spine may grow. One problem with this system is that the vertebrae of the spine may fuse spontaneously as a result of exposing the spine to fit the callipers.

Using the ISOLA® system, rods are inserted in a way that causes fusion of a small segment of spine proximally and distally to give a solid anchor for the rods. The rods do not control the sagital profile adequately and obtain their correction solely by distraction. In order to lengthen the rods to accommodate growth, the patient must be operated on every six months or so. The purpose of the pediatric ISOLA® is to stabilize the deformity. Definitive treatment of the scoliosis usually involves a further operation where vertebrae are fused together. Insertion of posterior growing rods and the final fusion procedure are relatively major surgical procedures especially if a thoracotomy is required for anterior release of the curve prior to insertion of the growing rods.

Factors for the development of early onset scoliosis vary considerably and include idiopathic and neuromuscular aetioligies.

Growth plates are affected by mechanical stimuli. Increased pressure on a growth plate reduces growth rate, whilst decreased pressure on a growth plate or traction can increase growth rate. Once a scoliosis curve develops the biomechanics of the spine are altered resulting in compression of the concave side of the curve and traction on the convex side of the curve. Growth on the concave side of the curve is therefore retarded whilst growth on the convex side is accelerated. The spine grows asymmetrically and the deformity is exacerbated.

In the condition known as "club foot", treatment aims are to: correct the deformity early, correct the deformity fully, and to hold the correction until growth stops. Two categories of the condition can be identified: those that are easy to correct, where correction is by splintage alone; and those that are resistant to correction, where response to splintage is poor and early operative correction is required.

Where the condition can be corrected by splintage, individual elements of foot rotation are corrected serially. In the Ponsetti method, the complex deformity is corrected by addressing each component in a defined order and only progressing to the next component when the previous has been adequately corrected. It would be useful to have a treatment which addressed all components simultaneously.

Operative correction requires the cutting of tendons and ligaments, which aside from post operative complications, tends to result in the foot being stiff in the long term.

It would therefore be desirable to develop apparatus, the use of which would improve outcomes for sufferers of conditions causing asymmetric growth.

SUMMARY OF THE INVENTION

According to one aspect of the invention, there is provided an implantable apparatus as specified in Claim 1.

According to another aspect of the invention, there is provided an implantable apparatus according to Claim 27.

According to another aspect of the invention, there is provided a kit of parts as specified in Claim 29.

According to another aspect of the invention, there is provided a method of treating immature people as specified in Claim 30.

According to another aspect of the invention, there is provided a method of treating mature patients as specified in Claim 32.

BRIEF DESCRIPTION OF THE DRAWINGS

In the drawings, which illustrate a preferred embodiment of the invention, and are by way of example:

FIG. 4b is an end view of a slide element designed to co-operate with the rod illustrated in FIG. 4a;

FIG. 5a is a schematic representation of the skeletal structure of a normal foot;

FIG. 5b is a schematic representation of the skeletal structure of a club foot;

FIG. 5c is a schematic representation of the lateral ray of foot bones;

FIG. 5d is a schematic representation of the medial ray of foot bones;

FIG. 7a is a slide element comprising a first part of a locking element;

FIG. 7b is a slide element comprising a second part of a locking element;

FIG. 7c is an end view of a screw;

FIG. 7d is a side view of the screw illustrated in FIG. 7c;

FIG. 7e is an end cap forming part of a locking element;

FIG. 7f is an end cap forming part of a locking element;

DETAILED DESCRIPTION OF THE PREFERRED EMBODIMENTS

Figure 1:
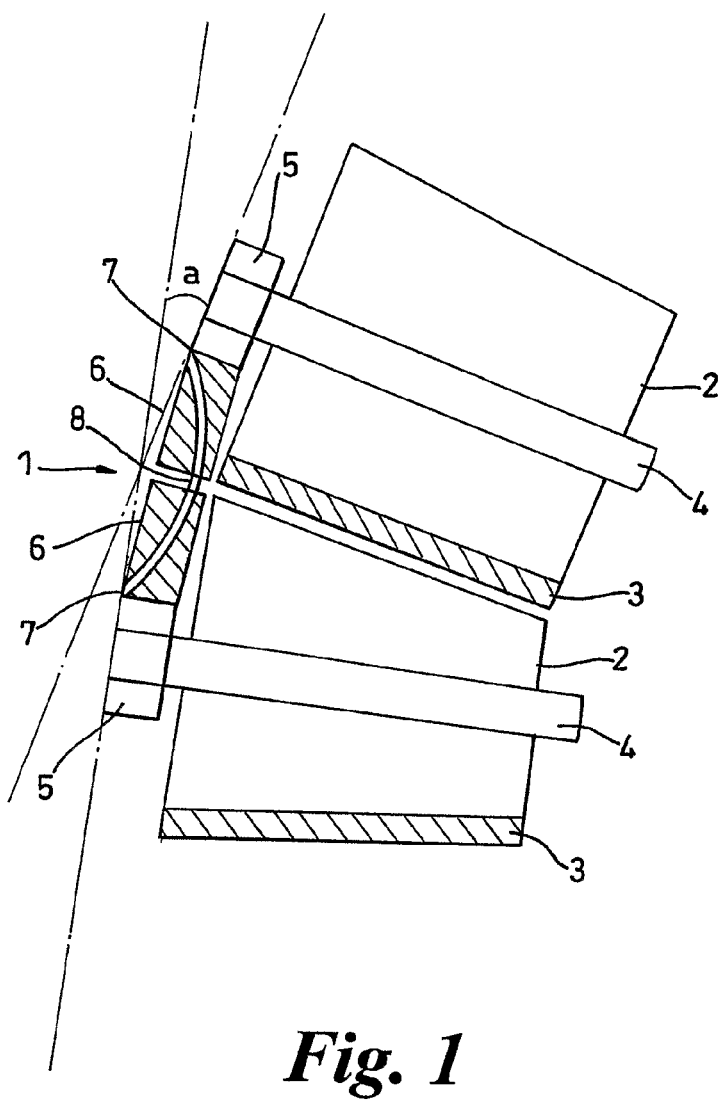
FIG. 1 is a front view of two adjacent vertebrae in a spine with a scoliosis curve having apparatus according to the invention attached thereto at the beginning of treatment.

Referring now to FIG. 1, a corrective apparatus is attached to adjacent vertebrae 2 of a spine with scoliosis. Each vertebrae 2 includes a growth plate 3. A screw 4 having a head 5 is attached to each of the vertebrae 2. A bore is first drilled through the vertebrae, and then the screw is inserted into the bore. The screws 4 are hydroxyapatite coated to provide a biological fix capable of being maintained over several years. The screws have a shallow thread depth and a long pitch. The shallow thread depth allows maximum screw strength for a given screw diameter and facilitates screw removal as each screw is over-drilled prior to removal. The only difference between the screw of apparatus 1 and screws currently used for attachment to bone lies in the head 5.

The screw head 5 is provided with attachment means for attachment of a slide element 6 including an internal bore 7 in which a rod 8 slides (see FIGS. 7a to 7f for a more detailed description.

The rod 8 is curved, the radius of curvature being calculated to correct the angle of curvature ∂ of the spine between the adjacent vertebrae shown. It will be noted that the slide elements 6 are set at an angle to the screw heads 5. The angle is ∂/2. This provides the maximum room for the rod 8, and therefore permits rods having smaller radii of curvature (i.e. more aggressive correction) than if the slide elements are on axis with the screw heads 5, and the angle of curvature ∂ is taken up by the rod 8 alone. As the child grows, the adjacent vertebrae grow resulting in the distance between the screws 4 increasing. As the slide elements 6 are attached to the screw heads 5, the distance between the two slide elements increases. Due to the fixation of the slide element to the screw head 5 and the screw 4 to the vertebrae 2, the vertebrae must move in an arc corresponding to the shape of the rod 8. This arcuate movement of the vertebrae 2 not only moves the vertebrae closer to a normal position, i.e. adjacent vertebrae lying on substantially on the same axis, but also further stimulates this corrective growth by reducing pressure on the growth plate 3 remote from the slide element 6. As mentioned above, growth is more rapid where the pressure on a growth plate is reduced. As pressure is reduced at one end of the growth plate 3, it is commensurately increased on the other side of that growth plate. The recovery to normal alignment of adjacent vertebrae is therefore enhanced.

Figure 2:
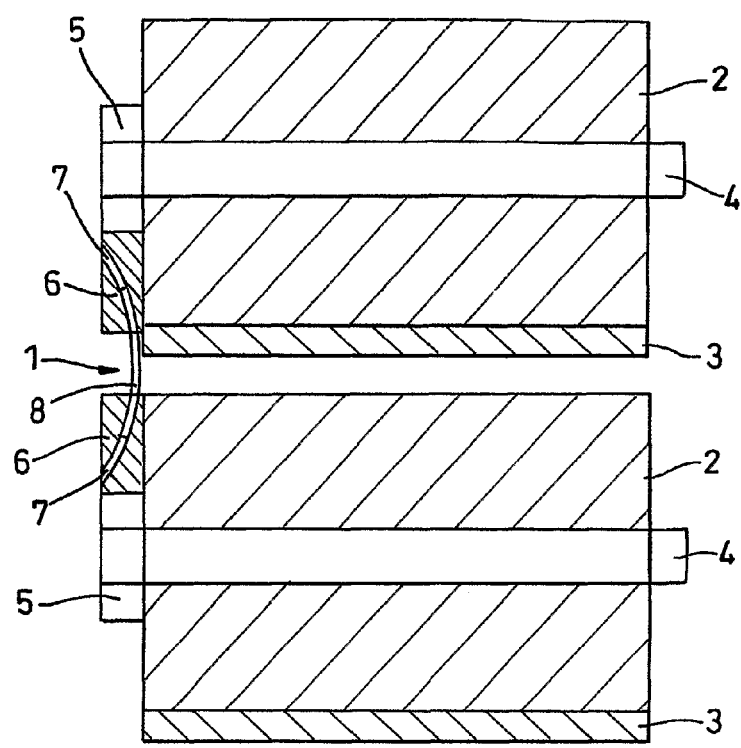
FIG. 2 is a front view of two adjacent vertebrae in a spine with a scoliosis curve having apparatus according to the invention attached thereto post treatment.

In FIG. 2, the apparatus has been in place for some time. As the child has grown, the distance between the screws 4 has increased, and only the ends of the rod 8 are located in the bores 7 in the slide elements 6. The scoliosis has been corrected.

Figure 3A:
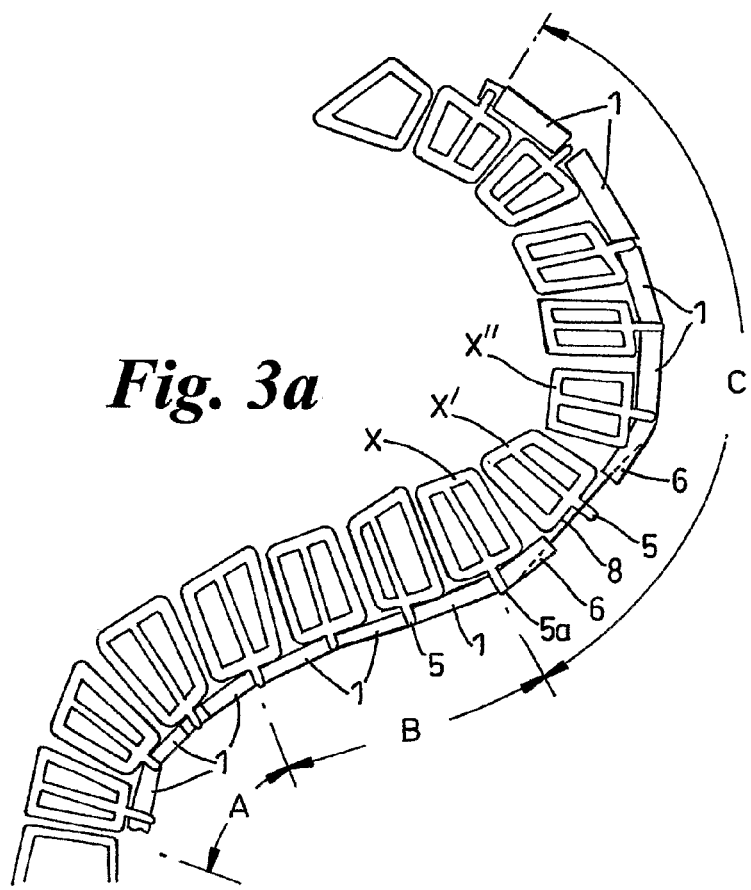
FIG. 3 is front view of a spine with a scoliosis curve having apparatus according to the invention attached to vertebrae of the spine.

Referring to FIG. 3, a spine with a scoliosis curve is fitted with apparatus 1, as shown in FIG. 1 and 2, between each adjacent vertebrae. The angle between adjacent vertebrae ranges between 0-5 degrees in the lower section A of the spine, 0 to 2 degrees in the mid section B, and 5 to 10 degrees in the upper section C of the spine. The curvature of any individual rod between adjacent vertebrae can be selected to match the degree of angular deformity at that location, thereby providing for much more refined treatment of scoliosis than is possible with apparatus of the prior art. Furthermore, by using an individual corrective rod for each pair of adjacent vertebrae, the force due to growth on any one screw 4 (fixation point) is only the force exerted by one growth plate, and therefore is comparatively small. If correction of a scoliosis using known apparatus which fix rods to the spine only at the top and bottom thereof were attempted, the fixation points proximally and distally rods would have to withstand the force due to growth generated by each of the growth plates, and would result in comparatively large forces on the fixation points. In the apparatus of the invention the force generated by each growth plate is harnessed locally in the construct spreading the forces on the screws 4 (the fixation elements) evenly.

Figure 3B:
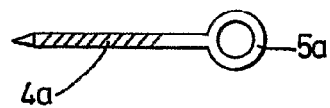

In FIG. 3, the vertebrae X and X" are separated by a vertebra X'. Apparatus 1 is fitted to the vertebrae X and X". Vertebra X' is fitted with an attachment (illustrated in FIG. 3b) comprising a threaded shank 4a and a head in the form of an eye 5a. The rod 8 slides in the eye 5a and a corrective force is exerted on the vertebra X'.

Figure 4A:
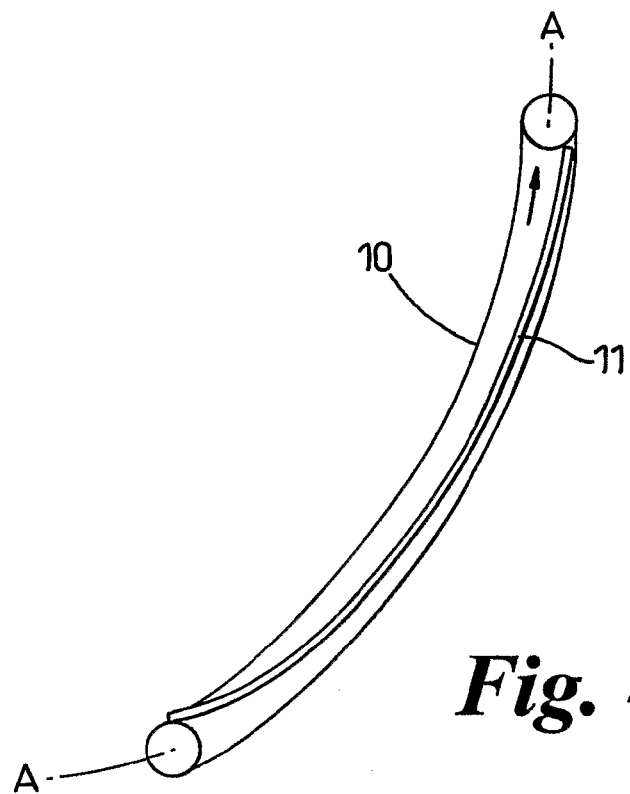
FIG. 4a is a schematic representation of a rod for apparatus according to another aspect of the invention.
Figure 4B:
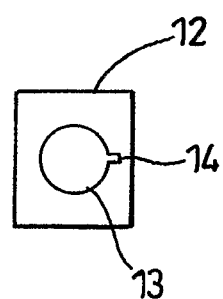

Referring to FIG. 4a, an alternative rod 10 is illustrated. As well as being curved, the rod 10 comprises a track 11. In FIG. 4b, there is shown a slide element 12. The bore 13 in which the rod 10 slides includes a channel 14 in which the track 11 slides. The track 11 has a pitch so that as the rod 10 is drawn out of the slide element 12 the rod is caused to rotate about its own axis A-A. This feature allows for the apparatus of the invention to correct rotational misalignment between adjacent vertebrae. As will be clear from FIG. 4a, in order to correct for rotational misaligment, there must be no rotational movement between the rod and the slide element in which the rod is located. As an alternative to a track running along a rod of substantially circular cross-section, the rod could have a non-circular cross-section, for example square, and this could run in a slide element having a correspondingly shaped bore. The rod 10 illustrated in FIG. 4a is marked at each end with indicia to tell the surgeon which way round the rod should be inserted. The arrow points towards the apex of the scoliosis.

FIGS. 5a to 5d assist in explaining how the apparatus of the invention can be used to correct skeletal misalignments other than in the spine. FIG. 5a illustrates a normal foot, where the bones of the lateral ray (see FIG. 5c) lie on an axis L-L, and the bones of the medial ray (see FIG. 5d) lie on an axis M-M. FIG. 5b illustrates a dub foot, where instead of all the bones of the lateral ray lying on the axis L-L, only the calcaneus 21 of the lateral ray lies on this axis, the cuboid 22 and metatarsal 23 lying on an axis L'-L' set at an angle Y to the axis L-L. In the case of the medial ray, instead of all the bones 24 to 27 thereof lying on the axis M-M, only the talus 24 of the medial ray lies on this axis. The navicular 25, the inner cuneiform 26 and the metatarsal 27 lie on an axis M'-M' set at an angle Z to the axis M-M. The misalignment of the lateral and medial rays of the club foot illustrated in FIG. 5b can be corrected by attaching the apparatus 1 illustrated in FIGS. 1 to 4 to the bones 21 and 22 of the lateral ray and bones 24 and 25 of the medial ray. The radius of curvature of the rod 8 and bores 7 must be selected to match the angle of misalignment Y or Z respectively. The forefoot supination pronation profile could be corrected by a rotational component built into the rod. The rotational misalignment between the talus and calcaneus in club foot could be corrected by an arrangement of the type illustrated in FIG. 4a, 4b is required. The relationship of the talus to the tibia could also be addressed.

As well as being used to correct misalignment between bones, the apparatus of the invention can also be used to correct some deformities occurring within a bone. For example, some conditions such as Perthes disease and developmental dysplasia of the hip (DDH) lead to rotation of the femur, which currently is corrected by breaking the femur, rotating one part of the broken femur relative to the other and rejoining the two parts of the bone. As part of treatment for various diseases reshaping the femur may be desirable.

Figure 6:
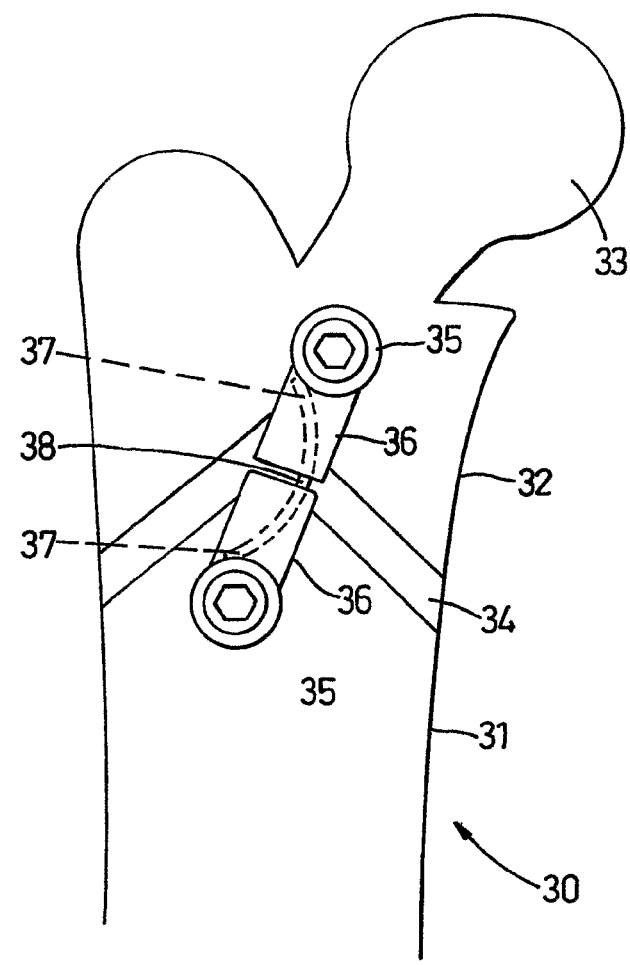
FIG. 6 illustrates the apparatus of the invention being used to correct a torsional deformity of the lower limb.

Instead of performing a varus derotation osteotomy the same effect could be obtained gradually using this device. As can be seen from FIG. 6, the femur 30 comprises an upper part 32 which includes the ball part 33 of the ball and socket hip joint, and a lower part 31. The lower and upper parts 31, 32 are either side of a growth plate 34. The apparatus of the invention can be used to generate a torsional force on the femur, which can be used to correct a developing torsional deformity. A screw 35 is inserted into each of the lower and upper parts 31, 32 of the femur. Attached to these screws are slide elements 36, each including a bore 37 in which a curved rod slides. As the child grows, the distance between the screws 35 increases and the shaped of the rod 38 causes a torsional force to be exerted on the lower part 31 with respect to the upper part 32 of the femur, thereby causing the deformity to be corrected. This use of the apparatus of the invention is particularly useful as the outcome of an osteotomy (breaking and re-setting a bone) is not always as successful as would be desirable. Also, in cases of minor deformity, such as rotational deformities in the lower limb, the risks of a major operation may be considered too great given the level of disability. The risks associated with fitting apparatus of the invention are very low, and therefore the invention could be used to treat patients having minor deformities.

FIGS. 7a to 7f illustrate a locking arrangement for locking a slide element to a screw. FIG. 7a illustrates a slide element 40. Extending from one end thereof is a first part of a locking element, which consists of a semi-circular portion 41 having a bore 42 located in its flat surface. FIG. 7b illustrates a second slide element 43. Extending from one end is the second part of the locking element, which consists of a semi-circular portion 44 having a protrusion 45 extending from its flat surface. The protrusion 45 is dimensions so as to mate with the bore 42. The main body 42a of the slide element 40 may be set at an angle to the semi-circular portion 41, and likewise the main body 44a of the slide element 43 may be set at an angle to the semi-circular portion 44. A range of slide elements may be produced, the angle between the main body and the semi-circular portion that engages with the screw head 48 being different. A slide element would then be selected to match the angular displacement of the bones whose position is to be corrected.

FIGS. 7c and 7d illustrate a screw 46 having a threaded shaft 47 and a head 48. A pair of slide elements 40, 43 is attached to the screw 46 illustrated in FIGS. 7c and 7d. When the protrusion 45 of the second locking element mates with the bore 42 of the first locking element, the two elements form a circular cross-section. The screw head 48 includes a semi-circular surface 51 upon which the outer surface of the first locking element rests. The first and second locking elements 41, 44 and hence the slide elements 40 and 43 of which they form a part ate held tightly in the screw head 48 by an externally threaded nut 50 which mates with an internally threaded wall 49 of the said screw head 48.

FIGS. 7e and 7f illustrate first and second end pieces 51 and 53 including a protrusion 52 and bore 54 respectively. The protrusion 52 of end piece 51 engages with the bore 42 of slide element 40, so that the slide element can be locked to a screw head 48 without the attachment of the slide element 43. Similarly, the protrusion 45 of the slide element 43 engages with the bore 54 of the end piece 53, so that the slide element 43 can be locked in place in a screw head.

Where the apparatus is being used to correct a torsional deformity, the screw head and the outer surfaces of the locking elements must not allow rotation therebetween. This could be achieved by making the semi-circular surfaces 42, 44 and the inner surface 55 of the screw head rectangular for instance.

Figure 8:
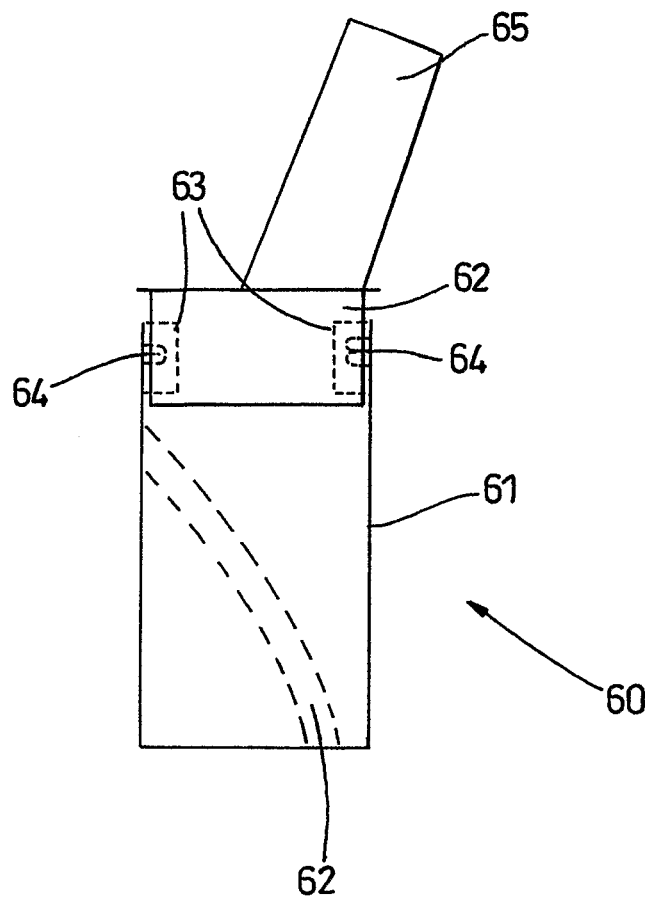
FIG. 8 is a side view of an alternative slide element.

FIG. 8 illustrates a slide element 60 including a bore 62 in which a rod may slide. The slide element 60 has a main body 61 and an end piece 62 mounted telescopically therein. The end piece 62 includes grooves 63 which engage with protrusions 64 to define the direction in which the end piece may move, and the extent of such movement The end piece 62 also mounts an element 65 which locks into a screw head in a similar manner to that illustrated in FIGS. 7a to 7f The apparatus is fitted to a patient such that the end-piece is fully extended. When the bones to which the apparatus is fitted ate under load, for example when standing, the end piece 62 slides into the main body 61. This ensures that the bones carry load, which is important to minimise stress shielding of the bone and reduce stresses on the implant.

The apparatus of the invention may be used on adults where no growth is expected, in which case the rods are fixed, rather than slidable, with respect to the screws fixed to the bones. The apparatus would typically be used in operations to fuse together vertebrae and its purpose would be to hold the spine in the desired shape whilst the vertebrae fused together.

Whereas the apparatus described with reference to FIG. 1 comprises a rod slidably mounted in adjacent slide elements, the apparatus illustrated in FIGS. 9a and 9b comprises a first element 100 which includes a bore 102 and a second element 101 which includes a rod 103. The rod 103 slides in the bore 102 and is attached to a block 104 which is itself attachable to a vertebrae in the same manner as illustrated in FIG. 1. A threaded bore 105 is provided in wall 106 of the first element 100, the threaded bore 105 receiving a grub screw 107 that is adjustable to either permit or prevent the rod 103 sliding in the bore 102. In use the first and second elements 100, 101 are attached to fixation points provided by fixation device, such as those illustrated in FIGS. 1 and 2. The second element 101 is typically attached to a fixation point below the fixation point to which the first element 100 in the bore 102 of which the rod 103 slides. As the person grows, the deformity is corrected due to the angle of curvature of the rod.

Once a defined amount of growth has occurred the corrective effect of the device may be reduced or removed by providing one or both ends of the rod with a taper which permits lateral movement between the rod and the bore in which it slides.

Figure 9A:
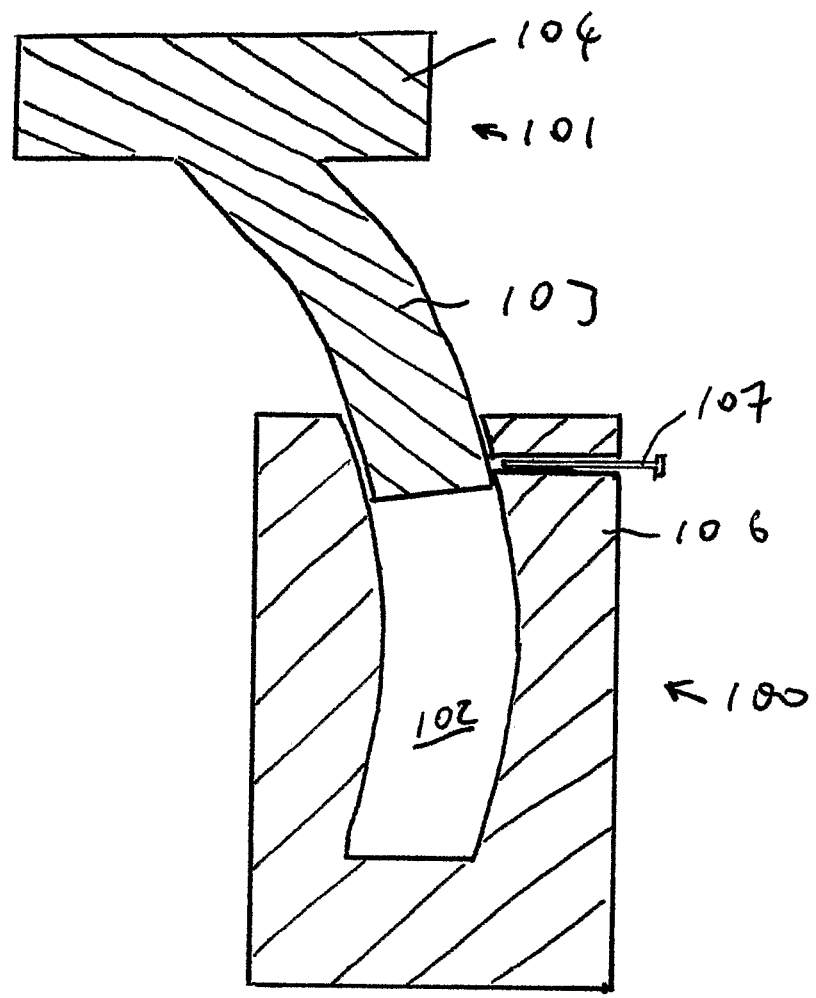
FIG. 9a is a schematic representation of another embodiment of an apparatus according to the invention in an extended configuration.
Figure 9B:
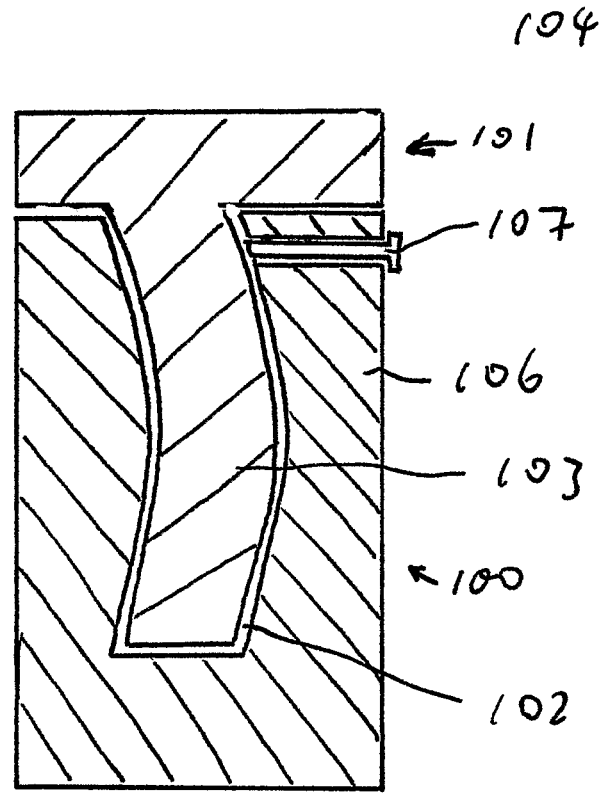
FIG. 9b is a schematic representation of the apparatus according to the invention in a retracted configuration.

With reference to FIGS. 1 and 2 and 9a an 9b, deformity correction is achieved by placing the device in under tension, that is adjacent vertebrae are brought together and the device fitted achieving as much correction as is possible at implantation, and then the residual deformity correction is achieved by 5 mm of growth at that motion segment. Deformity in the coronal plane and control of extent of kyphosis or lordosis (saggittal plane) is achieved by cutting the rod and bore(s) in an arc such that 5 mm movement along the circumference of the arc/circle would give the appropriate angular correction. Thus if 10 degrees correction was required with 5 mm movement:

10 degrees is 1/36 of a circle 5 mm is 1/36 of circumference of required circle 180 mm is circumference of circle required to give 10 degrees correction with 5 mm movement $2\Pi R$=circumference=180

R=180/2Π mm

Similarly any corrective angle can be calculated for a movement of a particular distance. Rotational correction is addressed by means of a spiral in the rod and bore (see FIGS. 4a and 4b).

The distances between the screws after insertion and tensioning would be expected to be about 2 cm in the thoracic spine and 3 cm in the lumbar spine in young adolescents and correspondingly smaller in younger children. The screw diameter used in the vertebral body would be as large as possible for maximum strength and need at least 12 mm of length in each rod to attach to the modular rod. (assuming 9 mm screw with 3 mm extra for locking mechanism) For a lordoscoliosis a few degrees of kyphosis would be desirable at each level and also a few degrees of rotation would be desirable.

With reference to FIGS. 1 to 3a and 9a and 9b, when correcting a deformity requiring the rod and slide element to move apart, the power of growth alone may not be sufficient in all cases to drive elongation of the implant so it may be necessary to insert a driver device in to the rod to push the two components of the device apart. This could take the form of a spring or an osmotic pressure device inserted into the lumen/bore of the outer rod and pushing on the end of the inner rod. The driver device would provide a continuous/constant pressure helping to elongate the device as growth occurred.

The device of the invention may also be used in the correction of scoliosis in skeletally mature patients. The correction of scoliosis with modern pedicle screw, hook, rod systems is achieved by loading the spine to reduce it to the desired configuration using a combination of stress relaxation of the tissues and flexibility of the deformity to achieve correction. These instrumentation systems do not however allow accurate segmental correction, eg the rod rotation technique does not derotate the spine but rather tends to rotate it more in the direction of the deformity.

The device of the invention described for use as a growing rod can be used as a means of accurately realigning spinal segments in adult scoliosis correction. The device is designed so that when it is extended it fits on to the deformed spine between adjacent vertebral fixation points, such as pedicle screws (see FIG. 9a). When the rod is compressed it shortens and realigns the segments to the desired configuration (FIG. 9b). It is then locked in this configuration using the grub screw 107. The realignment of the spinal segments can be performed in the coronal, saggittal and rotational planes simultaneously using this method. The device used at a particular level will give the required saggittal profile for that segment and derotate and compress the segment so as to achieve a near anatomical spinal alignment.

The device of the invention allows the spine to be realigned much more accurately on a segmental basis with derotation at each level. Moreover the spine could always be instrumented on the convex side first where the pedicles are larger and stronger and further away from the spinal cord. Segmental correction as described could give a better cosmetic result by derotating the ribs helping reduce the size of the residual rib hump and would allow each level to be adjusted several times to gain the maximum curve reduction by better utilising the stress relaxation properties of the spine. For example, using the embodiment illustrated in FIGS. 9a and 9b, the deformity between adjacent vertebrae could be corrected as far as is possible and the grub screw 107 tightened. The tissues around the vertebrae then relax permitting further correction of the deformity.

When used in the correction of deformity in skeletally mature patients the device may be made of titanium, which is the material commonly used in scoliosis implants, as the implant is used in a locked configuration and hence no bearing/movement is involved once the procedure has been completed. Also its bearing surfaces do not need to be highly polished (as they would need to be in the growing rod implant).

This implant system of the invention can be applied to the deformed spine and then gradually tensioned to slowly and systematically reduce the spinal deformity. This will make reduction of large curves easier as the difficulties with reducing the spine to the rod and the risk of implant pullout in that process will be greatly reduced. Thus the instrumented spine can be tensioned at each level and a gradual reduction achieved with avoidance of stress peaks on individual bone fixation points and more fully utilising the spine's stress relaxation properties. This technique may be of particular benefit in procedures where a vertebrectomy has been required. The implant would provide stability during the vertebrectomy and then allow a gradual controlled reduction.

The invention clamied is:

1. Implantable skeletal deformity correction apparatus, the apparatus comprising a curved rod, a pair of spaced apart attachment member, each of the attachment members being attachable to a bone, wherein each attachment member mounts a rod receiving member and the rod is mounted in the rod receiving members of each of the pair of spaced apart attachment members, wherein said rod is curved in the axial direction of the rod, and each rod receiving member comprises a bore curved in the axial direction of the bore, the curve corresponding to the curved rod such that post implantation of the apparatus the rod is free to slide along a predetermined path with respect to each of the rod receiving members, the apparatus being free of means configured to lock the rod with respect to the rod receiving members.

2. Implantable apparatus according to claim 1, wherein the rod and/or at least one of the rod receiving members comprise means to prevent rotation of the rod in the or each rod receiving member.

3. Implantable apparatus according to claim 2, wherein the means to prevent rotation of the rod in the or each rod receiving member comprises a track mounted on the rod, and an indent in the rod receiving member in which the track slides.

4. Implantable apparatus according to claim 3, wherein the track is formed in a spiral.

5. Implantable apparatus according to claim 3, wherein the rod is non-circular in cross-section and slides in a correspondingly shaped element.

6. Implantable apparatus according to claim 1, wherein the rod receiving member includes a plurality of sections, one being telescopically slidable with the other.

7. Implantable apparatus according to claim 6, wherein the sections include means to prevent rotation of one section relative to another.

8. Implantable apparatus according to claim 1, wherein the attachment member includes a head and the rod receiving member is attached to the head.

9. Implantable apparatus according to claim 1, wherein the attachment member is selected from the group consisting of: a screw, a bolt, a blade plate, a pedicle hook, and a laminar hook.

10. Implantable apparatus according to claim 1, further comprising means to retain the rod when it is slidably mounted in the rod receiving member.

11. Implantable apparatus according to claim 1, wherein the rod is curved in two planes.

12. Implantable apparatus according to claim 1, wherein the rod comprises an indicia indicating the direction the rod should be oriented.

13. Implantable apparatus according to claim 1, further comprising a guide member attachable to a bone, the guide member comprising an opening for receiving the rod.

14. Implantable apparatus according to claim 1, wherein at least one end of the rod is tapered.

15. Implantable apparatus according to claim 1, comprising a plurality of attachment members and a plurality of rods, each attachment member being attachable to a bone, and opposing ends of each rod being mounted in respective rod receiving members.

* * * * *